(12) United States Patent
Scampini et al.

(10) Patent No.: US 10,271,826 B2
(45) Date of Patent: Apr. 30, 2019

(54) SWAB ASSEMBLY FOR SPECIMEN COLLECTION

(71) Applicant: HOLOGIC, INC., Marlborough, MA (US)

(72) Inventors: Steven A. Scampini, Groton, MA (US); Ryan P. Oliva, Mendon, MA (US)

(73) Assignee: HOLOGIC, INC., Marlborough, MA (US)

( * ) Notice: Subject to any disclaimer, the term of this patent is extended or adjusted under 35 U.S.C. 154(b) by 686 days.

(21) Appl. No.: 13/738,225

(22) Filed: Jan. 10, 2013

(65) Prior Publication Data

US 2014/0194777 A1    Jul. 10, 2014

(51) Int. Cl.
*A61B 10/02* (2006.01)
*A61B 10/00* (2006.01)
*B01L 3/00* (2006.01)

(52) U.S. Cl.
CPC .......... *A61B 10/02* (2013.01); *A61B 10/007* (2013.01); *A61B 10/0045* (2013.01); *B01L 3/5029* (2013.01); *A61B 2010/0074* (2013.01); *A61B 2010/0216* (2013.01)

(58) Field of Classification Search
CPC . A61B 10/02; A61B 10/0045; A61B 10/0096; A61B 10/0291; A61B 2010/0216; A61B 2010/0074; A61B 2010/0067; A61B 10/0051; A61B 2019/307
USPC .............. 600/562, 569, 572; 206/205, 569
See application file for complete search history.

(56) References Cited

U.S. PATENT DOCUMENTS

| 3,388,043 A | | 6/1968 | Ingvorsen | |
|---|---|---|---|---|
| 3,712,296 A | * | 1/1973 | Gradone | 600/572 |
| 3,961,620 A | * | 6/1976 | Schack et al. | 600/570 |
| 4,027,658 A | * | 6/1977 | Marshall | A61B 10/02 600/570 |
| 4,136,680 A | * | 1/1979 | Southworth | A61B 10/02 435/304.1 |
| 5,246,856 A | * | 9/1993 | Gaarslev | 600/572 |
| 5,787,891 A | * | 8/1998 | Sak | 600/569 |
| 6,612,996 B2 | * | 9/2003 | Williams | 600/569 |

(Continued)

OTHER PUBLICATIONS

Cornell University Animal Health Diagnostic Center, "Technique for Culturing Mares and Stallions" Jun. 2012. Retrieved from <https://ahdc.vet.cornell.edu/docs/cem-culturing_contagious_equine_metritis.pdf> on Mar. 31, 2016.*

(Continued)

*Primary Examiner* — David J. McCrosky
(74) *Attorney, Agent, or Firm* — Vista IP Law Group LLP

(57) ABSTRACT

A swab assembly for collecting a specimen from a patient includes an elongated shaft having a proximal end, a distal end, and a notch between its proximal and distal ends; a sheath having a proximal end, a distal end, and a lumen extending between its proximal and distal ends, wherein a portion of the elongated shaft is disposed within the sheath lumen, and the sheath is slidable relative to the elongated shaft; and a collection tip coupled to the distal end of the elongated shaft and configured for obtaining the specimen. The sheath is slidable between a first position in which the shaft notch is disposed within the sheath lumen and wherein the sheath protects the elongated shaft from breaking at the notch, and a second position in which the shaft notch is exposed out of the sheath lumen.

5 Claims, 3 Drawing Sheets

(56) References Cited

U.S. PATENT DOCUMENTS

| | | |
|---|---|---|
| 2004/0260201 A1 | 12/2004 | Mueller, Jr. |
| 2005/0288606 A1 | 12/2005 | Alter |
| 2008/0077046 A1 | 3/2008 | Burg |
| 2009/0240164 A1* | 9/2009 | Gillespie ............ A61B 10/0291 600/569 |
| 2011/0021950 A1 | 1/2011 | Daniels |

OTHER PUBLICATIONS

PCT International Search Report and Written Opinion for PCT/US2013/078375, Applicant Hologic, Inc., Forms PCT/ISA/210, 220, and 237, dated Feb. 27, 2014 (12 pages).

* cited by examiner

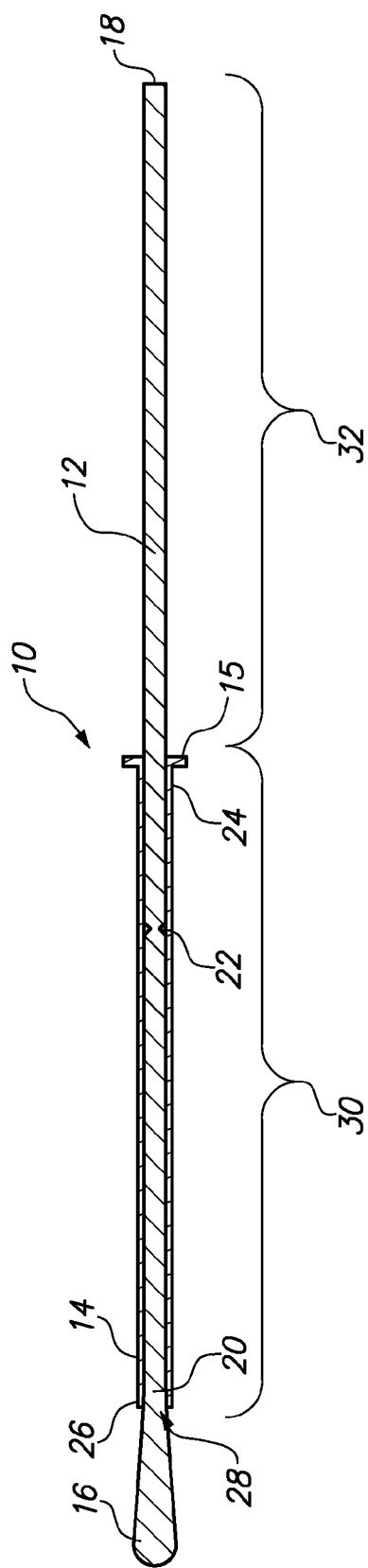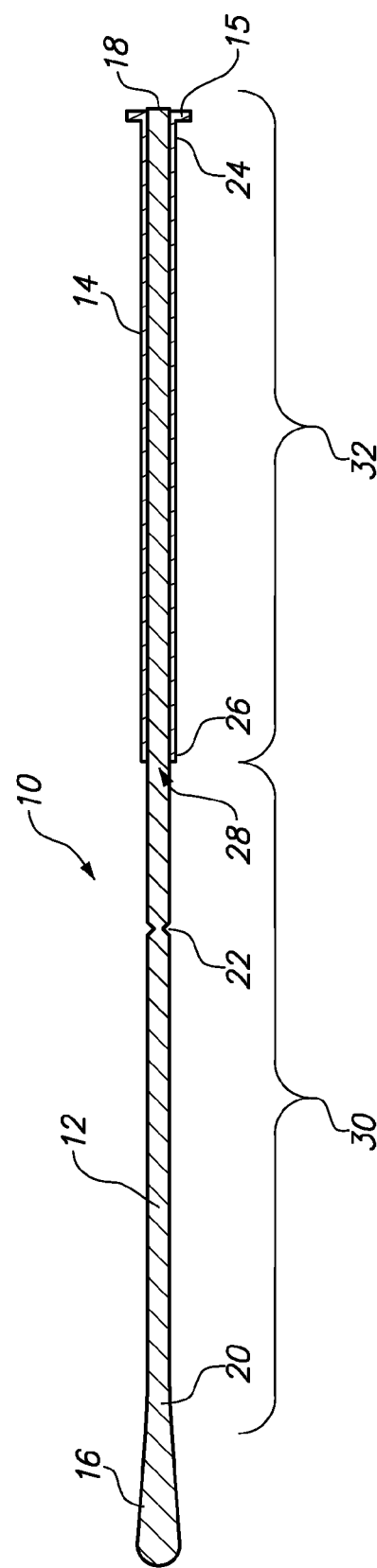

SWAB ASSEMBLY FOR SPECIMEN COLLECTION

FIELD OF INVENTION

The disclosed inventions pertain to devices used for biological specimen collection, and more particularly, to a swab assembly for collecting a biological specimen from a urethra, a cervix, or the like.

BACKGROUND

Currently, swabs are used for the collection of specimens to test for sexually transmitted diseases, or other biological testing. Such swabs may be used to collect specimens from the urethra or the cervix of a patient. A specimen collection swab may include an elongated shaft and a collection tip made of a fibrous or foam material. The elongated shaft may include a scored area to facilitate breaking the shaft at a desired height in order to fit the shaft and collection tip into a standard collection tube after the sample is obtained from the patient. However, a disadvantage associated with these collection swabs is that the scored area may cause the swab to prematurely break at the scored area during the sample collection process. Patient discomfort when collecting a specimen using the known collection swabs is also a problem.

SUMMARY

In accordance with one aspect of the disclosed inventions, a swab assembly for collecting a specimen from a patient is provided. The swab assembly may be sized and shaped for being inserted into a urethra or a cervix. In one embodiment, the swab assembly includes an elongated shaft having a proximal end and a distal end, the elongated shaft having a notch therein between its proximal and distal ends, such that the elongated shaft preferentially breaks at the notch when a force is applied to the elongated shaft. The swab assembly further includes a sheath having a proximal end and a distal end, the sheath defining a lumen extending between its proximal and distal ends, wherein at least a portion of the elongated shaft is disposed within the sheath lumen, with the sheath being slidable relative to the elongated shaft. A collection tip is coupled to the distal end of the elongated shaft and configured for obtaining the specimen. The elongated shaft may include a protrusion located proximally relative to the collection tip, wherein the protrusion is configured for preventing the sheath from moving over the collection tip. Alternatively, the sheath may be configured for covering the collection tip, such that the collection tip is compressed and disposed within the sheath lumen.

The sheath is slidable between a first position in which the shaft notch is disposed within the sheath lumen and wherein the sheath protects the elongated shaft from breaking at the notch, and a second position in which the shaft notch is exposed out of the sheath lumen, and wherein the sheath does not protect the elongated shaft from breaking at the notch. A length of the sheath may be less than a length of the elongated shaft, such that the elongated shaft extends through the entire length of the sheath lumen when the sheath is in the first position and in the second position. The collection tip may remain outside of the sheath lumen when the sheath is in the first position and in the second position.

In accordance with another aspect of the disclosed inventions, a method for collecting a specimen from a patient using the swab assembly is provided. The method includes the steps of inserting the swab assembly into a body lumen (e.g., a urethra or a cervix) of the patient until the collection tip is adjacent to a target collection site; obtaining the specimen by contacting the target collection site with the collection tip; removing the swab assembly from the body lumen, wherein the elongated shaft is disposed within the sheath lumen such that the notch remains positioned in the sheath lumen during the inserting, obtaining, and removing steps; sliding the sheath relative to the elongated shaft, or sliding the elongated shaft relative to the sheath, such that the shaft notch is disposed outside of the sheath lumen; and breaking the elongated shaft at or proximate the notch. The collection tip may be positioned distally relative to the sheath during all steps of the method. Alternatively, the method may include a further step of, before the step of obtaining the specimen, exposing the collection tip by sliding the sheath relative to the elongated shaft, or sliding the elongated shaft relative to the sheath, such that the notch remains positioned in the sheath lumen. It should be appreciated that the swab may be more easily inserted when the fibrous or foam tip is covered by the smooth sheath, due to reduced patient discomfort. Once inserted, the sheath is pulled back, exposing the tip for specimen collection.

Other and further aspects and features of the disclosed inventions will be evident from reading the following detailed description of embodiments thereof, which are intended to illustrate, not limit, the claimed inventions.

BRIEF DESCRIPTION OF THE DRAWINGS

The drawings illustrate the design and utility of embodiments of the disclosed inventions, in which similar elements are referred to by common reference numerals, and in which:

FIG. 1 is a cross-sectional view of a swab assembly in accordance with one embodiment, with a sheath in a first position;

FIG. 2 is a cross-sectional view of the swab assembly in FIG. 1 with the sheath in a second position;

DETAILED DESCRIPTION OF THE ILLUSTRATED EMBODIMENTS

Figure 3:
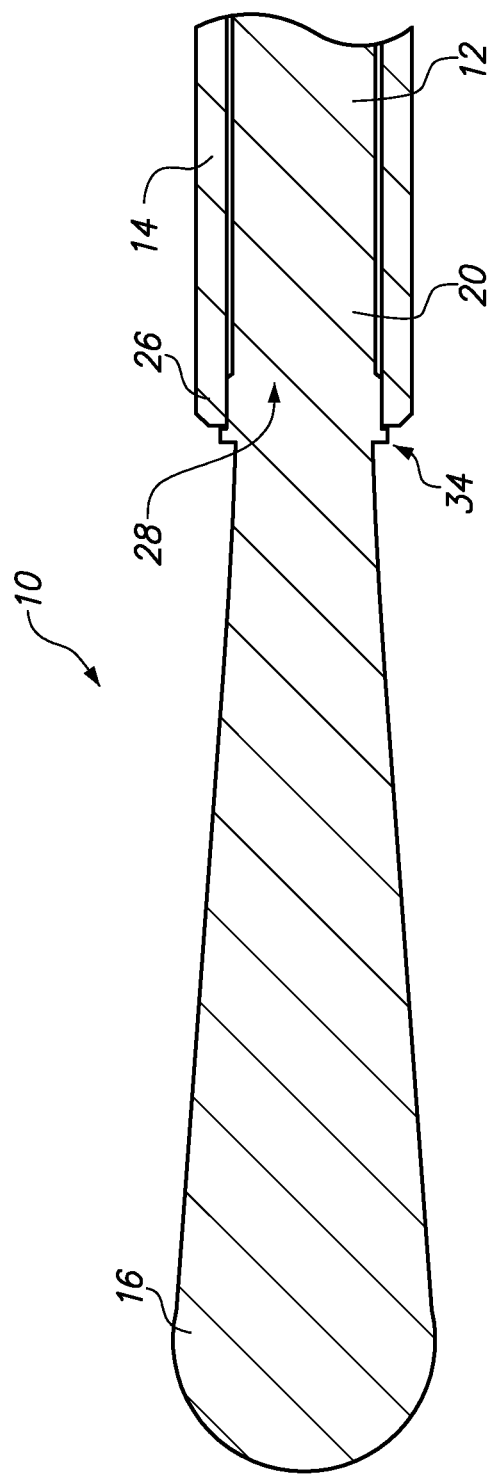
FIG. 3 is a cross-sectional view of a distal end of the swab assembly, in accordance with another embodiment.

Turning first to FIG. 1, an exemplary swab assembly 10 for collecting a specimen from a patient is shown. The swab assembly 10 may be sized and shaped for being inserted into a urethra or a cervix. The swab assembly 10 may be used for collecting cellular material that may be used to test for sexually transmitted diseases. The swab assembly 10 is preferably configured for collecting a specimen, while avoiding premature breakage.

The swab assembly 10 generally includes an elongated shaft 12, a sheath 14, and a collection tip 16. The elongated shaft 12 has a proximal end 18, a distal end 20, and a notch 22 between the proximal and distal ends 18, 20. The elongated shaft 12 is configured to preferentially break at the notch 22 when a force is applied to the elongated shaft 12.

The collection tip 16 is coupled to the distal end 20 of the elongated shaft 12, and is configured for obtaining the specimen. The collection tip 16 may be made of a fibrous or foam material. For example, the collection tip 16 may be similar to a collection tip of a cotton swab.

The sheath 14 has a proximal end 24 and a distal end 26. A sheath lumen 28 extends between the proximal and distal ends 24, 26 of the sheath 14. The sheath 14 may be made of a biocompatible material, and may have a low-friction external surface in order to minimize patient discomfort during insertion into a body lumen of the patient.

A portion of the elongated shaft 12 is disposed within the sheath lumen 28, and the sheath 14 is slidable relative to the elongated shaft 12. In particular, the sheath 14 is slidable between a first position, shown in FIG. 1, and a second position, shown in FIG. 2. When the sheath 14 is in the first position, the shaft notch 22 is disposed within the sheath lumen 28. Thus, the sheath 14 protects the elongated shaft 12 from breaking at the notch 22 when the sheath 14 is in the first position shown in FIG. 1. When the sheath 14 is in the second position, the shaft notch 22 is exposed outside of the sheath lumen 28. Thus, the sheath 14 does not protect the elongated shaft 12 from breaking at the notch 22 when the sheath 14 is in the second position shown in FIG. 2.

In the embodiment shown in FIGS. 1 and 2, the first position is a distal position and the second position is a proximal position. However, it should be well understood that, depending on the location of the notch 22, the length of the sheath 14, and/or the length of the elongated shaft 12, the sheath 14 may alternatively be in a proximal position or an intermediate position when the shaft notch 22 is disposed within the sheath lumen 28. In general, the sheath 14 is slidable between a position where the shaft notch 22 is covered by the sheath 14 and a position where the shaft notch 22 is disposed outside of the sheath 14.

The sheath 14 includes an enlarged handle portion 15 on the proximal end 24 of the sheath 14. The handle portion 15 may be grasped by the user when sliding the sheath 14 relative to the elongated shaft 12. Thus, the handle portion 15 facilitates sliding the sheath 14 back and forth on the elongated shaft 12. Alternatively, the sheath 14 does not include a handle portion 15, and instead has a constant outer diameter along its entire length. In this embodiment, the user may grasp the outer surface of the sheath 14 in order to the slide the sheath 14 relative to the elongated shaft 12.

The length of the sheath 14 is less than the length of the elongated shaft 12. As such, the elongated shaft 12 extends through the entire length of the sheath lumen 28 when the sheath 14 is in the first position and in the second position. In the example shown in FIGS. 1 and 2, a distal portion 30 of the elongated shaft 12 is disposed within the sheath lumen 28 when the sheath 14 is in the first position, and a proximal portion 32 of the elongated shaft 12 is disposed within the sheath lumen 28 when the sheath 14 is in the second position. The distal portion 30 of the elongated shaft 12 includes the notch 22, and the proximal portion 32 of the elongated shaft 12 does not include the notch 22.

In one embodiment, the elongated shaft 12 may include a positive engagement feature for limiting the movement of the sheath 14 relative to the elongated shaft 12. For example, as shown in FIG. 3, the elongated shaft 12 includes a protrusion 34 located proximally relative to the collection tip 16. The protrusion 34 is configured for preventing the sheath 14 from moving over the collection tip 16. Similarly, the elongated shaft 12 may include a protrusion in other locations along the length of the elongated shaft 12 in order to limit proximal or distal movement of the sheath 14 relative to the elongated shaft 12.

Figure 4:
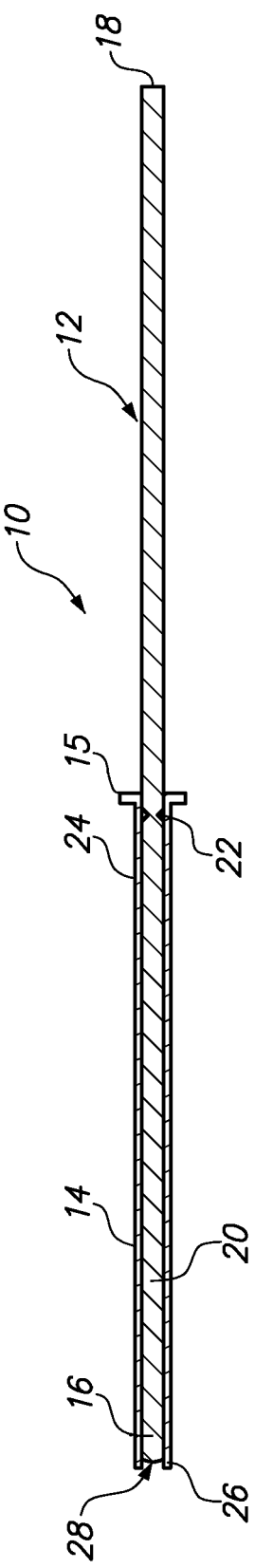
FIG. 4 is a cross-sectional view of the swab assembly in accordance with yet another embodiment, with the sheath disposed over a collection tip.

In the embodiments shown in FIGS. 1-3, the collection tip 16 remains outside of the sheath lumen 28 whether the sheath 14 is in the first position or the second position. Alternatively, the sheath 14 may be configured for being positioned over the collection tip 16, as shown in FIG. 4. In this embodiment, the sheath 14 may be slidable between three different positions. In the first sheath position, shown in FIG. 4, the collection tip 16 and the shaft notch 22 are positioned within the sheath lumen 28 while the swab assembly 10 is being inserted through a body lumen (e.g., a urethra, cervix, or the like). In the second sheath position, shown in FIG. 1, the collection tip 16 is disposed outside of the sheath lumen 28, and the shaft notch 22 is positioned within the sheath lumen 28 while the specimen is being collected on the collection tip 16. In the third sheath position, shown in FIG. 2, the collection tip 16 and the shaft notch 22 are positioned outside of the sheath lumen 28 after the specimen is collected so that the elongated shaft 12 can be broken at the notch 22 before being deposited into a sample tube. In the embodiment shown in FIG. 4, the sheath 14 compresses the collection tip 16 while the swab assembly 10 is inserted through the body lumen. Thus, the effective outer diameter of the swab assembly 10 is reduced in order to minimize patient discomfort during insertion through the body lumen of the patient. After the swab assembly 10 is positioned at or near the specimen collection site, the sheath 14 is moved proximally relative to the elongated shaft 12 and the collection tip 16 is deployed and expanded.

Figure 5:
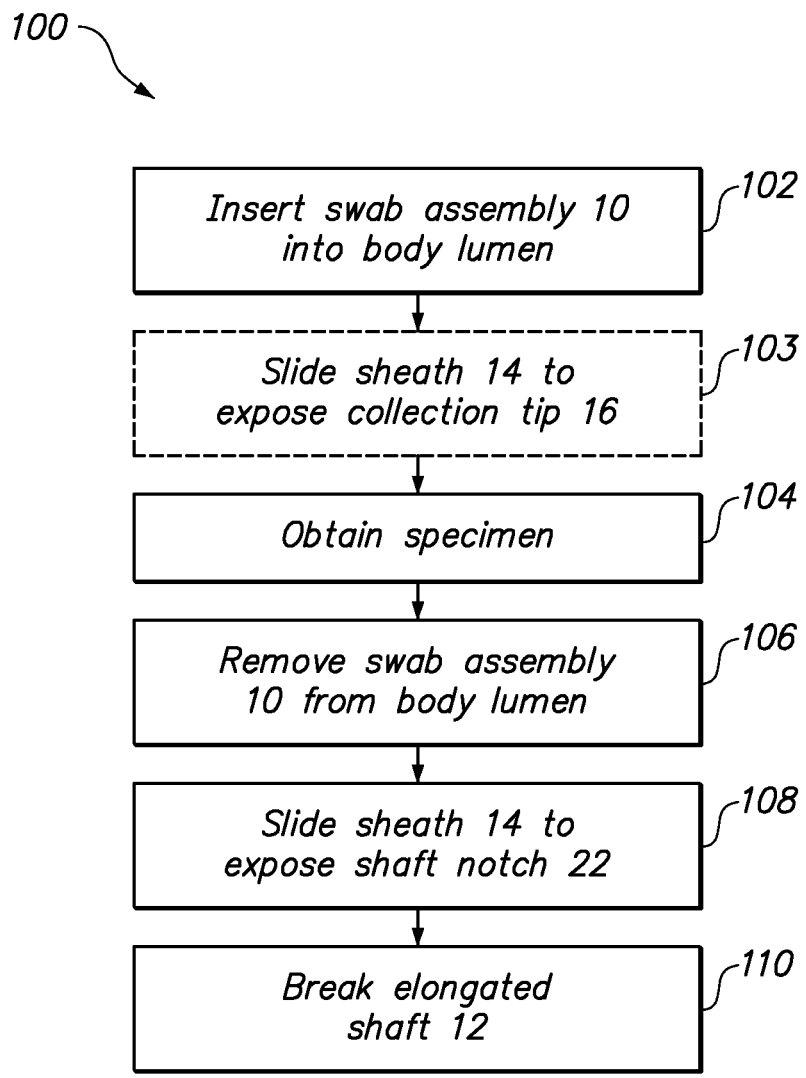
FIG. 5 is a flow chart illustrating a method for collecting a specimen using the swab assembly, in accordance with still another embodiment.

A method 100 for collecting a specimen from a patient using the swab assembly 10 is depicted in the flow chart shown in FIG. 5. In a first step 102, the swab assembly 10 is inserted into a body lumen of the patient until the collection tip 16 is adjacent to a target collection site. The body lumen may be, for example, a cervix or a urethra. Next, in step 104, the specimen is obtained by contacting the target collection site with the collection tip 16. The swab assembly 10 is then removed from the body lumen in step 106. The elongated shaft 12 is disposed within the sheath lumen 28 such that the notch 22 is positioned in the sheath lumen 28 during steps 102, 104, and 106. Next, in step 108, the sheath 14 is slid relative to the elongated shaft 12, or the elongated shaft 12 is slid relative to the sheath 14, such that the shaft notch 22 is disposed outside of the sheath lumen 28, as shown in FIG. 2. Finally, in step 110, the elongated shaft 12 is broken at or proximate the notch 22. In one embodiment of the method 100, the collection tip 16 is positioned distally relative to the sheath 14 during all steps of the method.

In another embodiment of the method 100, the collection tip 16 is positioned within the sheath lumen 28, as shown in FIG. 4, while the swab assembly 10 is inserted into the body lumen in step 102. In this embodiment, the method includes a step 103 of, before collecting the specimen, sliding the sheath 14 relative to the elongated shaft 12, or sliding the elongated shaft 12 relative to the sheath 14, such that the collection tip 16 is disposed outside of the sheath lumen 28 while the shaft notch 22 remains within the shaft lumen 28.

Again, because the fibrous or foam tip is covered by the smooth sheath during insertion, the patient experiences less discomfort. Once inserted, the sheath is pulled back, exposing the tip for specimen collection.

Although particular embodiments of the disclosed inventions have been shown and described, it will be understood that it is not intended to limit the disclosed inventions to the illustrated and described embodiments, and it will be obvious to those skilled in the art that various changes and modifications may be made without departing from the scope of the inventions, as defined by the claims.

What is claimed is:

1. A swab assembly for collecting a specimen from a human urethra, comprising:
   an elongated shaft having a proximal end and a distal end, the elongated shaft having a notch therein between its proximal and distal ends;
   a sheath having a proximal end and a distal end, the sheath defining a lumen extending between its proximal and distal ends, wherein at least a portion of the elongated shaft is disposed within the sheath lumen, and the sheath is slidable relative to the elongated shaft, the sheath being sized and shaped for insertion into a human urethra; and
   a compressible collection tip coupled to the distal end of the elongated shaft and configured for obtaining the specimen,
   wherein the sheath is slidable between a first position in which the shaft notch is disposed within the sheath lumen and wherein the sheath protects the elongated shaft from breaking at the notch, and a second position in which the shaft notch is exposed out of the sheath lumen, and wherein the sheath does not protect the elongated shaft from breaking at the notch,
   wherein the collection tip is configured to be compressed and positioned entirely within the sheath lumen during insertion of the sheath into the urethra, and
   wherein the collection tip expands when the collection tip is exposed out of the sheath lumen when the sheath is positioned at or near a specimen collection site within the urethra.

2. The swab assembly of claim 1, wherein the elongated shaft is configured to preferentially break at the notch when a force is applied to the elongated shaft.

3. A method for collecting a specimen from a human urethra using a swab assembly comprising a sheath having a lumen, an elongated shaft disposed within the sheath lumen, and a compressible collection tip coupled to a distal end of the elongated shaft, the collection tip having a length, wherein the elongated shaft comprises a notch configured to cause the elongated shaft to preferentially break at the notch when a force is applied to the elongated shaft, the method comprising the steps of:
   inserting the swab assembly into a human urethra until the collection tip is adjacent to a target collection site, wherein the collection tip is compressed and positioned within the sheath lumen during the inserting step;
   exposing the collection tip by sliding the sheath relative to the elongated shaft, or sliding the elongated shaft relative to the sheath, such that the notch remains positioned in the sheath lumen, and wherein the collection tip expands to a non-compressed state when exposed out of the sheath lumen;
   obtaining the specimen by contacting the target collection site with the collection tip;
   removing the swab assembly from the urethra, wherein the elongated shaft is disposed within the sheath lumen such that the notch is positioned in the sheath lumen during the inserting, obtaining, and removing steps;
   sliding the sheath relative to the elongated shaft, or sliding the elongated shaft relative to the sheath, such that the shaft notch is disposed outside of the sheath lumen; and
   breaking the elongated shaft at or proximate the notch.

4. A swab assembly for collecting a specimen from a human urethra, comprising:
   an elongated shaft having a proximal end and a distal end, the elongated shaft having a notch therein between its proximal and distal ends;
   a sheath having a proximal end and a distal end, the sheath defining a lumen extending between its proximal and distal ends, wherein at least a portion of the elongated shaft is disposed within the sheath lumen, and the sheath is slidable relative to the elongated shaft, the sheath being sized and shaped for insertion into a human urethra; and
   a compressible collection tip coupled to the distal end of the elongated shaft and configured for obtaining the specimen,
   wherein the sheath is slidable between a first position in which the shaft notch is disposed within the sheath lumen and wherein the sheath protects the elongated shaft from breaking at the notch, and a second position in which the shaft notch is exposed out of the sheath lumen, and wherein the sheath does not protect the elongated shaft from breaking at the notch,
   wherein the collection tip is configured to be compressed and positioned entirely within the sheath lumen during insertion of the sheath into the urethra, and
   wherein the collection tip expands when the collection tip is exposed out of the sheath lumen when the sheath is positioned at or near a specimen collection site within the urethra.

5. The swab assembly of claim 4, wherein the elongated shaft is configured to preferentially break at the notch when a force is applied to the elongated shaft.

* * * * *